(12) United States Patent
Blanchard

(10) Patent No.: US 11,186,581 B2
(45) Date of Patent: Nov. 30, 2021

(54) 2-(1,3-DIMETHYL-2,6-DIOXO-1,2,3,6-TETRAHYDRO-7H-PURIN-7-YL)-N-(6-(2-HYDROXYPHENYL)PYRIDAZIN-3-YL) ACETAMIDE AS A WNT PATHWAY MODULATOR

(71) Applicant: Agency for Science, Technology and Research, Connexis (SG)

(72) Inventor: Stephanie Eliane Blanchard, Nanos (SG)

(73) Assignee: AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 78 days.

(21) Appl. No.: 16/646,655

(22) PCT Filed: Sep. 11, 2018

(86) PCT No.: PCT/SG2018/050460
§ 371 (c)(1),
(2) Date: Mar. 12, 2020

(87) PCT Pub. No.: WO2019/054941
PCT Pub. Date: Mar. 21, 2019

(65) Prior Publication Data
US 2020/0270255 A1    Aug. 27, 2020

(30) Foreign Application Priority Data

Sep. 14, 2017  (SG) .......................... 10201707564X

(51) Int. Cl.
*A61K 31/522* (2006.01)
*C07D 473/08* (2006.01)
*C07D 487/04* (2006.01)

(52) U.S. Cl.
CPC .................................. *C07D 487/04* (2013.01)

(58) Field of Classification Search
CPC ........................... A61K 31/522; C07D 473/08
USPC ...................................... 514/263.34; 544/270
See application file for complete search history.

(56) References Cited

FOREIGN PATENT DOCUMENTS

WO    WO-2014/189466 A1    11/2014

OTHER PUBLICATIONS

Ho et al., "Scaffold Hopping and Optimization of Maleimide Based Porcupine Inhibitors," Journal of Medicinal Chemistry, vol. 60, pp. 6678-6692 (Jul. 2017).
Madan et al., "Wnt addiction of genetically defined cancers reversed by PORCN inhibition," Oncogene, vol. 35, pp. 2197-2207 (2016) (Published online Aug. 2015).

*Primary Examiner* — Douglas M Willis
(74) *Attorney, Agent, or Firm* — Foley & Lardner LLP

(57) ABSTRACT

The application relates to a 2,6-dioxo-purine derivative, 2-(1,3-dimethyl-2,6-dioxo-1,2,3,6-tetrahydro-7H-purin-7-yl)-N-(6-(2-hydroxyphenyl)pyridazin-3-yl)acetamide, and the use of this compound in the modulation of the Wnt pathway, and treating a disease or condition associated with Wnt pathway activity, such as cancer, a fibrotic disease, a degenerative disease or a metabolic disease.

13 Claims, 2 Drawing Sheets

2-(1,3-DIMETHYL-2,6-DIOXO-1,2,3,6-TETRAHYDRO-7H-PURIN-7-YL)-N-(6-(2-HYDROXYPHENYL)PYRIDAZIN-3-YL)ACETAMIDE AS A WNT PATHWAY MODULATOR

TECHNICAL FIELD

The invention relates to a Wnt pathway modulator, process for making it and methods for using it.

BACKGROUND

Wnt proteins are secreted glycoproteins acting as growth factors that regulate various cellular functions, including proliferation, differentiation, death, migration, and polarity, by activating multiple intracellular signalling cascades, including the β-catenin-dependent and -independent pathways. There are 19 Wnt members that have been found in humans and mice, and they exhibit unique expression patterns and distinct functions during development. In humans and mice, the 10 members of the Frizzled (Fz) family comprise a series of seven-pass transmembrane receptors that have been identified as Wnt receptors. In addition to Fz proteins, single-pass transmembrane proteins, such as low-density lipoprotein receptor-related protein 5 (LRP5), LRP6, receptor tyrosine kinase (RTK)-like orphan receptor 1 (Ror1), Ror2, and receptor-like tyrosine kinase (Ryk), have been shown to function as co-receptors for Wnt signalling. Therefore, it has been assumed traditionally that the binding of different Wnts to their specific receptors selectively triggers different outcomes via distinct intracellular pathways.

In the absence of Wnt signalling, β-catenin is bound and phosphorylated by a "destruction complex" containing the adenomatous polyposis coli (APC) and Axin proteins, as well as glycogen synthase kinase 3 (GSK3) and casein kinase I (CKI). Phosphorylated β-catenin is bound by the F box protein Slimb/β-TrCP and polyubiquitinated, leading to proteosomal degradation. In addition, the complex acts to prevent nuclear localization of β-catenin. Upon Wnt binding to Frizzled (Fz) and low-density lipoprotein-related proteins 5 and 6 (LRP5/6), GSK3, Axin, and other destruction complex components are recruited to the receptor complex. The function of the destruction complex is inhibited, and unphosphorylated β-catenin accumulates in the cytoplasm and eventually translocates to the nucleus. There, it associates with TCF proteins, converting TCF from a repressor into an activator of Wnt-responsive gene transcription.

Deregulation of components of Wnt/p-catenin signalling is implicated in a wide spectrum of diseases including degenerative diseases, metabolic diseases, and a number of cancers such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumor and medulloblastoma. Wnt signalling plays a role both during development, and within stem cell niches in adults. This is best established in skin, hematopoietic stem cells, mammary gland and in intestinal proliferation. For example, high level expression of DKK1, an inhibitor of Wnt signalling, blocks normal stem cell proliferation in mouse intestines, suggesting there is an essential role for Wnt signalling in maintenance of stem cells in the digestive tract. The role of Wnt in self renewal and expansion of stem cells has also been demonstrated for embryonic and neural stem cells, suggesting that Wnt signalling may be a general requirement of stem cell maintenance.

Inhibition of Wnt signalling, e.g., by overexpression of axin or an extracellular Wnt-binding protein, sFRP, reduces hematopoietic stem cell (HSC) growth in vitro and the ability to reconstitute HSCs in vivo. Notably, while overexpression of activated β-catenin can expand HSC populations in culture for extended periods, two groups have reported that β-catenin is not required for HSC survival and serial transplantation, supporting the proposal that there is more to Wnt signalling than stabilization of β-catenin in jtem cell survival. Diverse Wnts can regulate stem cell proliferation: Wnts 1, 5a, and 10b are able to stimulate expansion of HSC populations and Wnt5a acts synergistically with stem cell factor (SCF) to expand and promote self-renewal of HSCs. The demonstration of a role for Wnt5a in HSC self-renewal and its ability to synergize with stem cell factor is particularly interesting because Wnt5a often acts in a β-catenin independent manner. While Wnt signalling is critical for stem cell maintenance, it may therefore be via signalling pathways distinct from or in parallel to the β-catenin pathway.

Wnt/β-catenin signalling pathway is essential to embryonic development in general and organ morphogenesis, so it is not surprising that dysregulation of this pathway in adult has been linked to fibroblast biology and fibrosis. It has been demonstrated that Wnt/β-catenin signalling play a role in severe fibrotic diseases, such as pulmonary fibrosis, liver fibrosis, skin fibrosis and renal fibrosis.

Dysregulation of Wnt/β-catenin signalling contributes also to the development of diabetic retinopathy by inducing retinal inflammation, vascular leakage, and neovascularization. The binding of Wnt proteins to plasma membrane receptors on mesenchymal cells induces the differentiation of these cells into the osteoblast lineage and thereby supports bone formation. Wnts are also key signalling proteins in joint remodeling processes. Active Wnt signalling contributes to osteophyte formation and might have an essential role in the anabolic pattern of joint remodeling that is observed in ankylosing spondylitis and osteoarthritis. In contrast, blockade of Wnt signalling facilitates bone erosion and contributes to catabolic joint remodeling, a process that is observed in rheumatoid arthritis.

There is therefore a need to develop improvements in compounds that modulate or inhibit Wnt activity so as to, more effectively, treat diseases associated with Wnt activity.

SUMMARY

In one aspect, there is provided a compound of the following formula:

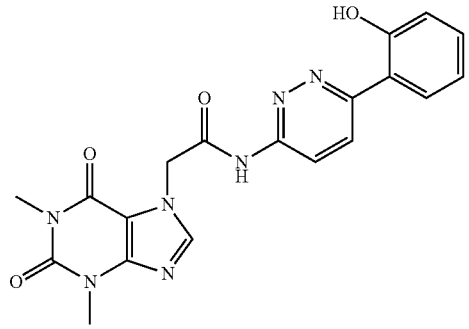 [SMILES: Cn1c(=O)c2c(ncn2CC(=O)Nc2ccc(-c3ccccc3O)nn2)n(C)c1=O]

or a pharmaceutically acceptable salt, solvate or prodrug thereof.

The compound of the present invention unexpectedly has good oral bioavailability and pharmacokinetic properties.

In one aspect, there is provided a compound as defined herein or a pharmaceutically acceptable salt, solvate or prodrug thereof for use as a medicament.

In one aspect, there is provided a method of modulating Wnt secretion and/or porcupine activity comprising exposing cells to a compound as defined herein or a pharmaceutically acceptable salt, solvate or prodrug thereof.

The cells may be cells that over-express Wnt protein. The method may be an in vitro method or it may be an in vivo method. Without wishing to be bound by theory, the inventors hypothesise that the compound as defined herein inhibits the secretion of Wnt proteins. The compound of the invention is capable of inhibiting porcupine, which is essential and specific for the palmitoylation of Wnt proteins before secretion.

In another aspect, there is provided a method of treating a disease or condition associated with Wnt pathway activity comprising administering to a subject in need thereof a therapeutically effective amount of a compound as defined herein or a pharmaceutically acceptable salt, solvate or prodrug thereof.

In another aspect, there is provided a compound as defined herein or a pharmaceutically acceptable salt, solvate or prodrug thereof for use in the treatment of a disease or condition associated with Wnt pathway activity.

In another aspect, there is provided the use of a compound as defined herein or a pharmaceutically acceptable salt, solvate or prodrug thereof in the manufacture of a medicament for the treatment of a disease or condition associated with Wnt pathway activity.

In another aspect, there is provided a pharmaceutical composition comprising a compound as defined herein or a pharmaceutically acceptable salt, solvate or prodrug thereof.

DETAILED DESCRIPTION

Figure 1:
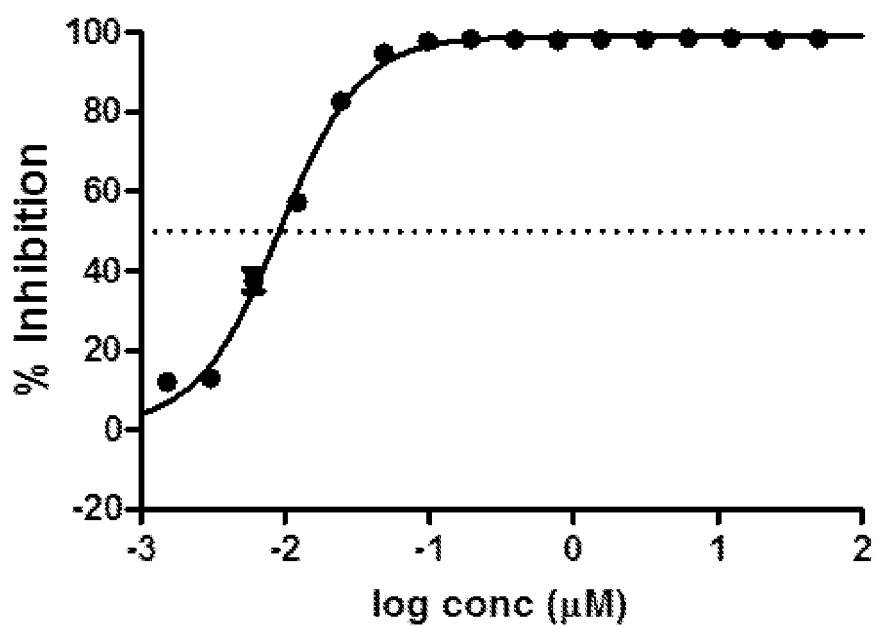
FIG. 1 shows the inhibition-dose titrations of Compound 1 in STF3A cells. The inhibition-dose titration allows the $IC_{50}$ values for Compound 1 to be determined, which is summarized in Table 1.
Figure 2:
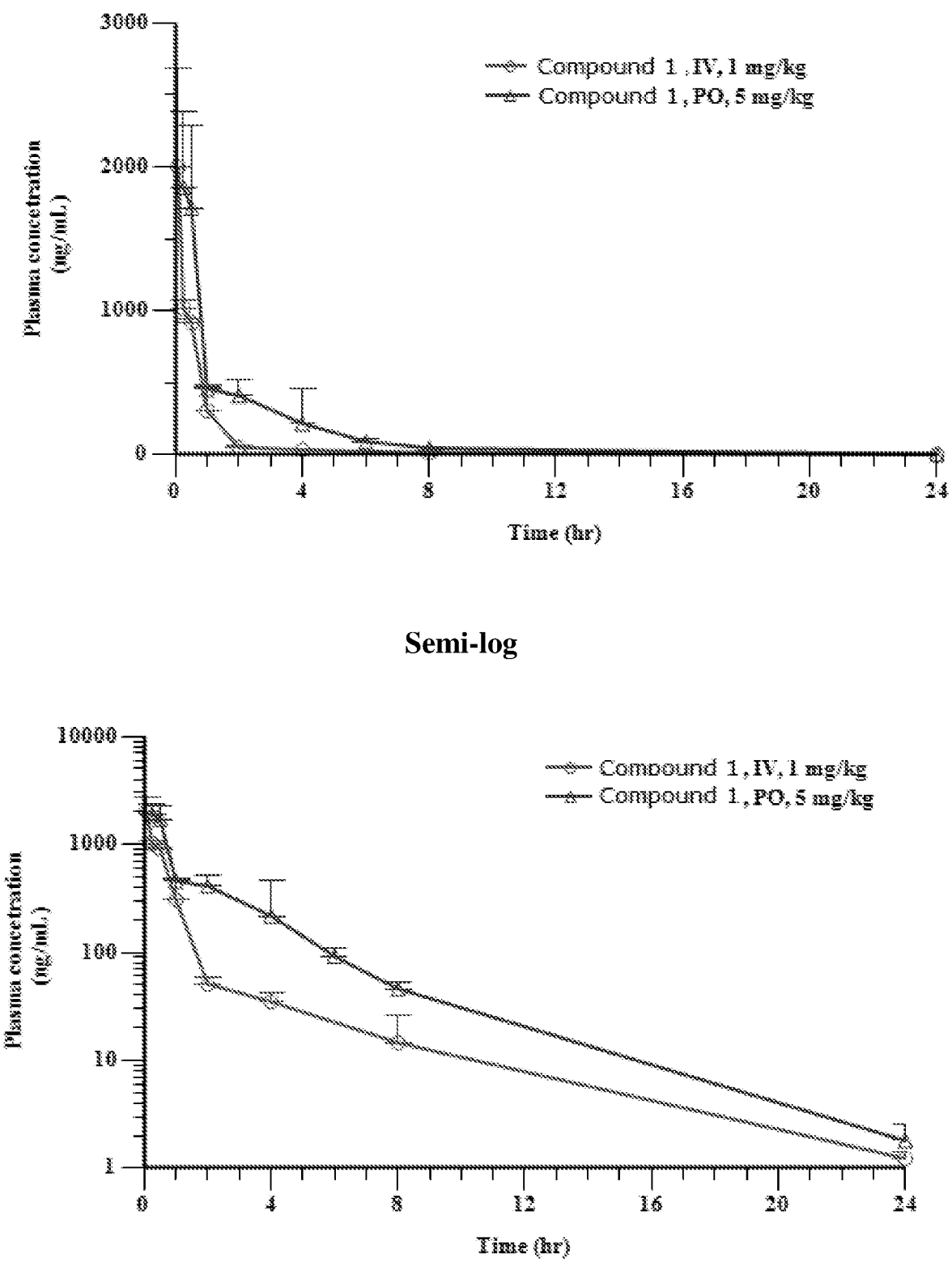
FIG. 2 shows the mean plasma concentration-time profile of Compound 1 in plasma following a single intravenous (Dose: 1 mg/kg) and oral (Dose: 5 mg/kg) administration in male BALB/c mice

The invention relates to the preparation and the use of a new compound that modulate Wnt activity, to methods of using the compound, as a single agent or in combination, for treating or preventing diseases and conditions associated with Wnt pathway activity, in particular having a dysfunction linked to Wnt signalling pathway i.e. cancer, fibrosis, stem cell and diabetic retinopathy. Thus the invention relates to a compound that act as modulators of the Wnt pathway and to pharmaceutical compositions comprising this compound and to its use for the preparation of a medicament for the treatment of diseases having a dysfunction linked to Wnt signalling pathway where Wnt plays a role in proliferation of cancer via multiple mechanisms, including a key role in stem cell maintenance. Dysfunction of the Wnt pathway is related to conditions including, but not limited to, cancers such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumour and medulloblastoma and other diseases with high Wnt expression such as fibrosis (including skin, idiopathic pulmonary, liver, renal interstitial, myocardial, infarct and liver) and diabetic retinopathy. Respiratory conditions, or respiratory tumours, may in certain embodiments not be conditions treated by the present invention.

Provided herein is a compound of the following formula:

(Compound 1)

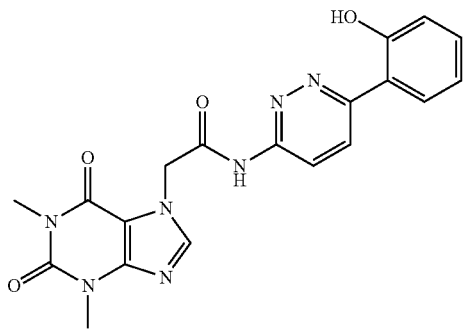 [SMILES: Cn1c(=O)c2c(ncn2CC(=O)Nc2ccc(-c3ccccc3O)nn2)n(C)c1=O]

or a pharmaceutically acceptable salt, solvate, or prodrug thereof.

The compound of the present invention unexpectedly has good oral bioavailability and pharmacokinetic properties. This is contrary to expectations that the pharmacokinetic properties of the compound to be poor due to its phenol moiety. Further, it is found that when the hydroxyl moiety is in an ortho position, the compound of the present invention is sufficiently able to reach systemic circulation after being orally administered without it being metabolised in the gastrointestinal tract, metabolised in the blood and cleared by the hepatic portal system (i.e. liver). Without being bound by theory, the phenolic group in the ortho position may be chelated (in vivo) and therefore unavailable for conjugation (phase 2 metabolism).

The compound of the present invention is characterized with $IC_{50}$ against STF3A of less than about 10 micromolar. In one embodiment, the $IC_{50}$ is less than 0.01 micromolar. A suitable method for testing $IC_{50}$ is as follows: approximately 5000 cells in 75 μl culture media are seeded in each well of black 96 well plates and incubated overnight at 37° C. 25 μl of serially diluted compound is then added to the cells giving final concentration. After 1 day of treatment, 100 μl of a luminescent cell viability assay reagent is added to each well and incubated for 10 minutes at room temperature. Luminescence is then measured to determine $IC_{50}$.

The compound may be such that it does not modulate, or does not inhibit, TRPA1. It may not inhibit TRPA1 at an $IC_{50}$ of about 10 micromolar or of about 5 micromolar or of about 2 micromolar or of about 1 micromolar. It may be a TRPA1 non-inhibitor. The term "not inhibit" in this context may refer to an inhibition of less than about 10%, or less than about 5, 2 or 1% at the specified concentration.

The compound of the present invention may inhibit phosphorylation of co-receptor LRP6 in PA-1 teratocarcinoma cells and/or in HPAF-II pancreatic adenocarcinoma cells by greater than about 40% after 4 hours at a concentration of about 2 micromolar. In this context, inhibition of 40% indicates that the concentration of phosphorylated LRP6 after 4 hours is 40% lower than in a control to which no inhibiting compound was added. The inhibition under the specified conditions may be greater than about 40%, or greater than about 45, 50 or 55%, and may be for example about 40, 45, 50, 55 or 60%. The inhibition may be achieved with a concentration of less than about 3 micromolar, or less than about 2, 1, 0.5, 0.2, 0.1 or 0.05 micromolar, or at a concentration of between about 0.003 and 2 micromolar, or between about 0.003 and 1.5 micromolar, 0.003 and 1 micromolar, 0.003 and 0.5 micromolar, 0.003 and 0.2 micromolar, 0.003 and 0.1 micromolar, 0.003 and 0.05, 0.003 and 0.01, 0.01 and 2, 0.1 and 2, 1 and 2, 0.01 and 0.1, 0.01 and 1, 0.01 and 0.1 and 0.05 or 0.005 and 0.5 micromolar, e.g. at a concentration of about 0.003, 0.005, 0.01, 0.002, 0.05, 0.1, 0.2, 0.5, 1, 1.5 or 2 micromolar.

The compound of the present invention includes all tautomers of the compound.

By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

For instance, suitable pharmaceutically acceptable salts of compound according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compound of the invention. Suitable pharmaceutically acceptable salts of the compound of the present invention therefore include acid addition salts.

S. M. Berge et al. describe pharmaceutically acceptable salts in detail in J. Pharmaceutical Sciences, 1977, 66:1-19. The salts can be prepared in situ during the final isolation and purification of the compound of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

The term "pro-drug" is used in its broadest sense and encompasses those derivatives that are converted in vivo to the compound of the invention. Such derivatives would readily occur to those skilled in the art, and include, for example, compounds where the free hydroxy group may be converted into an ester, such as an acetate or phosphate ester. Procedures for esterifying, eg. acylating, the compound of the invention are well known in the art and may include treatment of the compound with an appropriate carboxylic acid, anhydride or chloride in the presence of a suitable catalyst or base. A particularly preferred prodrug is a disodium phosphate ester.

The compound of the invention may be in crystalline form either as the free compound or as solvates (e.g. hydrates) and it is intended that both forms are within the scope of the present invention. Methods of solvation are generally known within the art.

In one embodiment, there is provided a compound as defined herein or a pharmaceutically acceptable salt, solvate or prodrug thereof for use as a medicament.

In one embodiment, there is provided a method of modulating Wnt secretion and/or porcupine activity comprising exposing cells to a compound as defined herein or a pharmaceutically acceptable salt, solvate or prodrug thereof.

In one embodiment, the modulating may be inhibiting.

In one embodiment, there is provided a method of treating a disease or condition associated with Wnt pathway activity comprising administering to a subject in need thereof a therapeutically effective amount of a compound as defined herein or a pharmaceutically acceptable salt, solvate or prodrug thereof. The subject may be human or may be non-human, e.g. a non-human mammal or other non-human animals.

In one embodiment, there is provided a compound as defined herein or a pharmaceutically acceptable salt, solvate or prodrug thereof for use in the treatment of a disease or condition associated with Wnt pathway activity.

In one embodiment, there is provided the use of a compound as defined herein or a pharmaceutically acceptable salt, solvate or prodrug thereof in the manufacture of a medicament for the treatment of a disease or condition associated with Wnt pathway activity.

The disease or condition may be a cancer, such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumor or medulloblastoma. The disease or condition may be a fibrotic disease, such as pulmonary fibrosis, liver fibrosis, skin fibrosis or renal fibrosis. It may be a degenerative disease. It may be a metabolic disease such as diabetic retinopathy. The disease or condition may also be a proliferative disorder. The disease or condition may also be stem cell retinopathy, rheumatoid arthritis, psoriasis or myocardial infarction.

In one embodiment, the disease or condition is a cancer characterized by abnormal Wnt activity. In one embodiment, the disease or condition is a cancer characterized by high Wnt activity.

The compound of the present invention may be made as exemplified in the Examples provided herewith.

In the development of a drug in solid state form suitable for scale up and cGMP production and ultimately for clinical and commercial use, an acceptable level of drug activity against the target of interest is only one of the important variables that must be considered. For example, in the formulation of pharmaceutical compositions it is imperative that the pharmaceutically active substance be in a form that can be reliably reproduced in a commercial manufacturing process and which is robust enough to withstand the conditions to which the pharmaceutically active substance is exposed.

In a manufacturing sense it is important that during commercial manufacture the manufacturing process of the pharmaceutically active substance be such that the same material is reproduced when the same manufacturing conditions are used. In addition it is desirable that the pharmaceutically active substance exists in a solid form where minor changes to the manufacturing conditions do not lead to major changes in the solid form of the pharmaceutically active substance produced. For example it is important that the manufacturing process produce material having the same crystalline properties on a reliable basis and also produce material having the same level of hydration.

In addition it is important that the pharmaceutically active substance be stable both to degradation, hygroscopicity and subsequent changes to its solid form. This is important to facilitate the incorporation of the pharmaceutically active ingredient into pharmaceutical formulations. If the pharmaceutically active substance is hygroscopic ("sticky") in the sense that it absorbs water (either slowly or over time) it is almost impossible to reliably formulate the pharmaceutically active substance into a drug as the amount of substance to be added to provide the same dosage will vary greatly depending upon the degree of hydration. Furthermore variations in hydration or solid form ("polymorphism") can lead to changes in physico-chemical properties, such as solubility or dissolution rate, which might in turn lead to inconsistent oral absorption in a patient.

Accordingly, chemical stability, solid state stability, and "shelf life" of the pharmaceutically active agent are very important factors. In an ideal situation the pharmaceutically active agent and any compositions containing it, should be capable of being effectively stored over appreciable periods of time, without exhibiting a significant change in the physico-chemical characteristics of the active component such as its activity, moisture content, solubility characteristics, solid form and the like.

Disclosed herein are also compositions for the modulation of Wnt activity, optionally for the treatment of a disease or condition associated with Wnt pathway activity. These incorporate the compound as defined above, together with one or more pharmaceutically acceptable adjuvants, diluents and/or carriers.

In one embodiment, there is provided a pharmaceutical composition comprising a compound as defined herein or a pharmaceutically acceptable salt, solvate or prodrug thereof. The pharmaceutical composition may further comprise one or more pharmaceutically acceptable carriers, diluents or adjuvants.

The compound of the present invention may be administered as compositions either therapeutically or preventively. In a therapeutic application, compositions are administered to a patient already suffering from a disease, in an amount sufficient to cure or at least partially arrest the disease and its complications. The composition should provide a quantity of the compound or agent sufficient to effectively treat the patient.

The therapeutically effective dose level for any particular patient will depend upon a variety of factors including: the disorder being treated and the severity of the disorder; activity of the compound or agent employed; the composition employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would commonly be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

In general, suitable compositions may be prepared according to methods which are known to those of ordinary skill in the art and accordingly may include a pharmaceutically acceptable carrier, diluent and/or adjuvant.

These compositions can be administered by standard routes. In general, the compositions may be administered by the parenteral (e.g., intravenous, intraspinal, subcutaneous or intramuscular), oral or topical route. More preferably administration is by the parenteral route.

The carriers, diluents and adjuvants must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The oral formulation may be formulated with one or more pharmacologically acceptable ingredients to make a tablet or capsule etc. with an enteric coating. Methods for such formulations are well known to those skilled in the art (see e.g., Remington: The Science and Practice of Pharmacy, $19^{th}$ ed. (1995) Mack Publishing Company, Easton, Pa.; herein incorporated by reference). The enteric coating may be an enteric coating which enhances delivery of the composition or active(s) drugs to specific regions of the gastrointestinal tract for enhanced bioavailability, such as are described in United States of America Patent Application Publication No. 20040162263 entitled "Pharmaceutical formulations targeting specific regions of the gastrointestinal tract" to Sands et al and published 19 Aug. 2004.

EXAMPLES

The following example provides a compound according to the present invention together a general synthetic scheme for preparing the compound. The person skilled in the art will readily appreciate the variations required to the illustrated example of the synthetic scheme in order to prepare other related compounds.

Examples 1

Synthesis of Compound 1

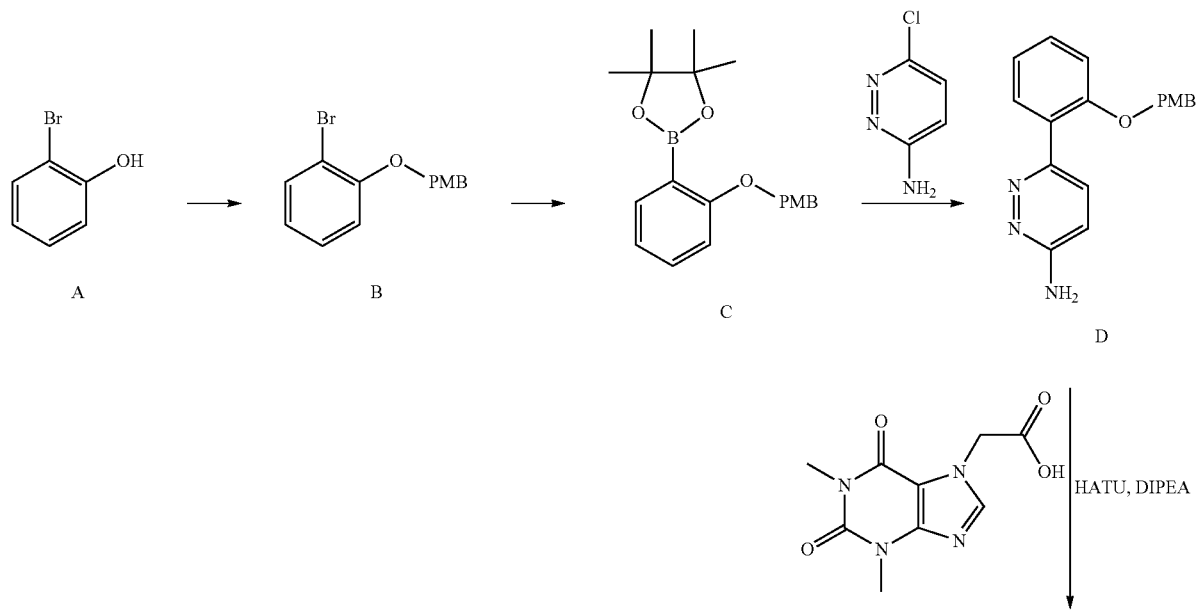

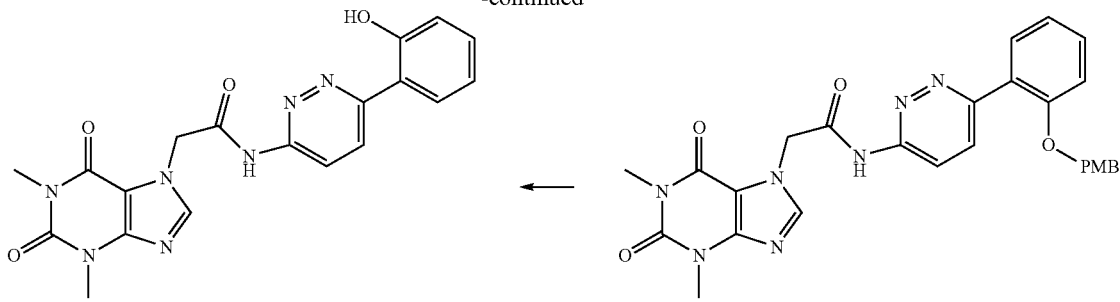

Compound 1 ← E

Step-1: 1-bromo-2-((4-methoxybenzyl)oxy)benzene

To a stirred solution of 2-bromophenol (3 g, 0.0173 mol), in acetonitrile (30 mL) was added K$_2$CO$_3$ (4.07 g, 0.0294 mol) followed by drop-wise addition of PMB-Cl (2.6 mL, 0.0193 mol). The reaction mixture was allowed to reflux for 19 h. The TLC analysis confirms the completion of starting material, reaction mass was filtered, washed with ethyl acetate and concentrated under reduced pressure. The residue obtained was dissolved in ethyl acetate (150 mL), washed with water (2×30 mL) and brine solution (20 mL), dried over sodium sulphate and concentrated under reduced pressure to get the title compound as pale brown solid.
Yield: 4 g (80%).

Step-2: 2-(2-((4(4-methoxybenzyl)oxy)phenyl)-4,4,5,5-tetramethyl-1,3,2-dioxaborolane A mixture of 1-bromo-2-((4-methoxybenzyl)oxy)benzene (1 g, 0.00341 mol) was added bis(pinacolato)diboron (0.953 g, 0.00375 mol), KOAc (1 g, 0.01023 mol) and dioxane (20 mL) was purged with argon for 15 min, followed by the addition of PdCl$_2$.dppf (0.125 g, 0.00017 mol). The mixture was allowed to reflux for 18 h. TLC analysis confirmed the completion of SM, reaction mass was filtered through a celite-bed, washed with ethyl acetate and concentrated under reduced pressure. The residue obtained was dissolved in ethyl acetate, washed with water (2×20 mL), brine solution (20 mL), dried over sodium sulphate and concentrated under reduced pressure to get the crude product. The crude product thus obtained was purified by column chromatography over silica gel (0-20% of ethyl acetate in pet.ether) as pale brown solid.
Yield: 0.7 g (60%).

Step-3: 6-(2-((4-methoxybenzyl)oxy)phenyl)pyridazin-3-amine

A mixture of 2-(2-((4-methoxybenzyl)oxy)phenyl)-4,4,5,5-tetramethyl-1,3,2-dioxaborolane (0.7 g, 0.0020 mol) and Cl pyridazine (0.265 g, 0.0020 mol) in dioxane:water (2.5:1) was added K$_3$PO$_4$ (1.27 g, 0.006 mol), degassed with N$_2$ for 15 minutes and then PdCl$_2$.dppf (73 mg, 0.0001 mol) was added. The reaction mixture was heated at 102° C. and stirred for 18 h. The reaction mixture was cooled to room temperature and DCM (200 mL) was added. The organic layer was separated, washed with water (3×10 mL), brine (10 mL), dried over anhydrous Na$_2$SO$_4$ and evaporated under vacuum. The crude product was purified by silica chromatography (230-400 mesh) by eluting with ethyl acetate in pet.ether (0-50%) to get the title product with 61% purity as brown solid which was proceeded for next step without further purification.

Yield: 350 mg (55%).
LCMS: 308.2 (M+H)$^+$

Step-4: 2-(1,3-dimethyl-2,6-dioxo-1,2,3,6-tetrahydro-7H-purin-7-yl)-N-(6-(2-((4-methoxybenzyl)oxy)phenyl)pyridazin-3-yl)acetamide To a stirred solution of 6-(2-((4-methoxybenzyl)oxy)phenyl)pyridazin-3-amine (0.3 g, 0.00097 mol) and 2-(1,3-dimethyl-2,6-dioxo-1,2,3,6-tetrahydro-7H-purin-7-yl)acetic acid (0.232 g, 0.00097 mol) in dry dichloromethane was added HATU (0.737 g, 0.00194 mol) followed by DIPEA (0.375 g, 0.00291 mol) at 0° C. and was allowed to warm to RT stirred for overnight. Reaction was monitored by TLC. The mixture was concentrated under reduced pressure, water (10 mL) was added to the residue, precipitated solid was filtered and purification by column chromatography over silica gel (0-4% of MeOH in DCM) provided the title compound as off-white solid.
Yield: 325 mg (63%).
$^1$H NMR (400 MHz, DMSO-d$_6$): δ 3.20 (s, 3H), 3.47 (s, 3H), 3.73 (s, 3H), 5.12 (s, 2H), 5.36 (s, 2H), 6.91 (d, J=8.80 Hz, 2H), 7.13 (t, J=15.20 Hz, 1H), 7.30 (d, J=8.40 Hz, 1H), 7.35 (d, J=8.40 Hz, 2H), 7.46-7.50 (m, 1H), 7.75-7.77 (m, 1H), 8.07-8.10 (m, 2H), 8.17 (s, 1H), 11.70 (s, 1H).
LCMS: 528.0 (M+H)$^+$

Step-5: 2-(1,3-dimethyl-2,6-dioxo-1,2,3,6-tetrahydro-7H-purin-7-yl)-N-(6-(2-hydroxyphenyl)pyridazin-3-yl)acetamide To a stirred solution of 2-(1,3-dimethyl-2,6-dioxo-1,2,3,6-tetrahydro-7H-purin-7-yl)-N-(6-(2-((4-methoxybenzyl)oxy)phenyl)pyridazin-3-yl)acetamide (0.3 g, 0.00057 mol) in dichloromethane at 0° C. was added TFA (0.22 ml, 0.00285 mol) and the reaction mixture was warmed to room temperature and was allowed to stir for 18 h. Reaction was monitored by LCMS. The mixture was concentrated under reduced pressure and the residue was diluted with water. Solid thus obtained was filtered, washed with 10% NaHCO$_3$ solution and further purified by prep HPLC to get the title compound as off-white solid.
Yield: 30 mg (13%).
$^1$H NMR (400 MHz, DMSO-d$_6$): δ 3.21 (s, 3H), 3.47 (s, 3H), 5.38 (s, 2H), 6.97-7.02 (m, 2H), 7.34-7.38 (m, 1H), 7.93 (d, J=9.36 Hz, 1H), 8.10 (s, 1H), 8.36-8.38 (m, 1H), 8.46 (d, J=9.60 Hz, 1H), 11.78 (s, 1H), 12.25 (s, 1H).
LCMS: 408.0 (M+H)$^+$

Materials and Methods

Cell Lines and Culture Conditions

HEK293-STF cell line was modified from Human embryonic kidney cell line HEK293 transfected with the STF reporter. HEK293-STF3 A cell line was further modified from HEK293-STF cell line to express Wnt3A. This cell line was used to identify compounds that regulate either early or late signalling components of the Wnt pathway. L-Wnt3 A (ATCC, #CRL-2647) cell line was used for providing Wnt3 A conditioned media. The three cell lines were grown in DMEM (Dulbecco's Modified Eagle Medium) with 10% FBS (fetal bovine serum) incubated in 37° C. with 5% $CO_2$.

Cell Viability Assay 5000 cells in 75 µl culture media were seeded in each well of black 96 well plates (Greiner #655090) and incubated overnight at 37° C. 25 µl of serially diluted compound was added to the cells giving final concentration of 50 µM to 1.5 nM. After 1 day of treatment, 100 µl of CellTiter-Glo® Luminescent Cell Viability Assay reagent (#G7571, Promega) was added to each well and incubated for 10 minutes at room temperature. Luminescence was measured using Tecan Safire2® microplate reader.

STF3A Assay $2 \times 10^4$ HEK293-STF3A cells in 75 µl culture media were seeded in each well of white 96 well plates (Greiner #655098) and incubated overnight at 37° C. 25 µl serially diluted compound was added to the cells to give final concentration of 50 µM to 1.5 nM. After 1 day of treatment, 100 µl of Steady-Glo® Luciferase Assay reagent (#E2520, Promega) was added to each well and incubated for 10 minutes at room temperature. Luminescence was measured using Tecan Safire2® plate reader.

Example 2

The objective of this study was to investigate the plasma pharmacokinetics of Compound 1 in male BALB/c mice following a single intravenous and oral dose administration. A group of eighteen male mice were divided in to two groups as Group 1 and Group 2 with nine mice in each group.

Animals in Group 1 were administered intravenously with Compound 1 solution formulation in 7.5% NMP, 5% Solutol HS-15 and 87.5% normal Saline at a dose of 1 mg/kg.

Animals in Group 2 were administered orally with Compound 1 solution formulation in 7.5% NMP, 5% Solutol HS-15 and 87.5% normal Saline at a dose of 5 mg/kg.

Blood samples (approximately 60 µL) were collected under light isoflurane anesthesia from retro orbital plexus at predose, 0.08, 0.25, 0.5, 1, 2, 4, 8 and 24 hr (IV) and predose, 0.25, 0.5, 1, 2, 4, 6, 8 and 24 hr (PO). During each sampling point, blood samples were collected in labeled pre-chilled tubes containing $K_2EDTA$ (20% $K_2EDTA$ solution) as an anticoagulant and protease inhibitor (10 µL of 10× solution/100 µL of blood). Low temperature was maintained till storage of plasma at −70° C. Plasma samples were separated by centrifugation of whole blood and stored below −70° C. until bioanalysis. All samples were processed for analysis by protein precipitation using acetonitrile (ACN) and analyzed with fit-for-purpose LC/MS/MS method (Lower limit of quantitation (LLOQ: 1.02 ng/mL). Pharmacokinetic parameters were calculated using the non-compartmental analysis tool of Phoenix WinNonlin® (Version 6.3). The overall pharmacokinetic parameters are summarized below:

TABLE 1

Structures and $IC_{50}$ activities on STF3A cells

| Compound No. | Structure | Example/ Comparator | $IC_{50}$ (µM) | Bioavailability |
|---|---|---|---|---|
| 1 | *structure* | Example | 0.009 | 42% |
| 2 | *structure* | Comparator | >10 | N/A |

| Route | Dose (mg/kg) | $T_{max}$ (hr) | $^aC_o/C_{max}$ (ng/mL) | $AUC_{last}$ (hr * ng/mL) | $AUC_{inf}$ (hr * ng/mL) | $T_{1/2}$ (hr) | CL (mL/min/kg) | $V_{ss}$ (L/kg) | % $F^b$ |
|---|---|---|---|---|---|---|---|---|---|
| IV | 1 | — | 2747.53 | 1480.60 | 1487.95 | 4.24 | 11.20 | 1.20 | — |
| PO | 5 | 0.25 | 1856.61 | 3108.35 | 3116.66 | 3.26 | 26.74 | 7.55 | 42 |

*$T_{1/2}$ expressed as $T_{1/2z}$, CL expressed as $CL_f$ and $V_{ss}$ expressed as $V_z$ for PO group
$^a$back extrapolated conc. for i.v. group;
$^b AUC_{last}$ was considered for calculating oral bioavailability Following a single intravenous dose administration of Compound 1 to male BALB/c mice, compound showed low plasma clearance (11.20 mL/min/kg; normal liver blood flow in mice is 90 mL/min/kg) with terminal elimination half-life of 4.24 hr. The Vss was ~2-fold more than normal volume of total body water (0.7 L/kg). Following a single oral administration of Compound 1 to male BALB/c mice at 5 mg/kg, plasma concentrations were quantifiable up to 24 hr (2 Animals out of 3) with $T_{max}$ at 0.25 hr. Oral solution bioavailability was 42%.

Example 3

The objective of the study is to determine the plasma pharmacokinetics of Compound 1 in male BALB/c mice following a single intravenous (1 mg/kg) and oral (5 mg/kg) administration in presence of a protease inhibitor.

The test compound: Compound 1 (Mol Wt: 407.39; Purity: 97.00%; Lot/Batch No.: Batch #1).

Test System

Healthy male BALB/c mice (8-12 weeks old) weighing between 25 to 30 g were procured from Global, India. Three mice were housed in each cage. Temperature and humidity were maintained at 22±3° C. and 30-70%, respectively and illumination was controlled to give a sequence of 12 hr light and 12 hr dark cycle. Temperature and humidity were recorded by auto-controlled data logger system. All the animals were provided laboratory rodent diet (Envigo Research private Ltd, Hyderabad). Reverse osmosis water treated with ultraviolet light was provided ad libitum.

Study Design

A group of eighteen male mice were divided in to two groups as Group 1 and Group 2 with nine mice in each group. Animals in Group 1 were administered intravenously with Compound 1 solution formulation in 7.5% NMP, 5% Solutol HS-15 and 87.5% normal Saline at a dose of 1 mg/kg. Animals in Group 2 were administered orally with Compound 1 solution formulation in 7.5% NMP, 5% Solutol HS and 87.5% normal Saline at a dose of 5 mg/kg.

The dosing volume administered was 5 mL/kg for intravenous and 10 mL/kg for oral administration. The assignment of animals is shown in the table below:

| Group | Route | Animal ID (Total) |
|---|---|---|
| 1 | IV | 9 (1-9) |
| 2 | PO | 9 (10-18) |

Formulation Preparation

The strength of intravenous and oral solution formulation was 0.2 and 0.5 mg/mL respectively.

| Ingredients | IV (0.2 mg/mL) | PO (0.5 mg/mL) |
|---|---|---|
| Compound 1 | 0.72 mg | 2.37 mg |
| NMP (7.5%) | 0.262 mL | 0.345 mL |
| Solutol HS-15 (5%) | 0.175 mL | 0.230 mL |
| Normal saline (87.5%) | 3.055 mL | 4.023 mL |

IV Formulation: Accurately weighed 0.72 mg of Compound 1 was transferred to a labelled bottle. To this bottle 0.262 mL of NMP, 0.175 mL of solutol HS-15 was added and vortexed after each addition. A volume 3.055 mL of normal saline was added and vortexed. Final formulation was vortexed for 2 minutes to obtain clear solution.

PO Formulation: Accurately weighed 2.37 mg of Compound 1 was transferred to a labelled bottle. To this bottle 0.345 mL of NMP, 0.230 mL of solutol HS-15 was added and vortexed after each addition. A volume 4.023 mL of normal saline was added and vortexed. Final formulation was vortexed for 2 minutes to obtain clear solution.

Formulation Results

After preparation of formulation, a volume of 200 µL was aliquoted for analysis. The formulation was analyzed which was within the acceptance criteria (in-house acceptance criteria is ±20% from the nominal value). Formulation was prepared freshly prior to dosing.

| Compound | Formulation | Theoretical Conc. (mg/mL) | Conc. Found (mg/mL) | % Change |
|---|---|---|---|---|
| 1 | IV | 0.20 | 0.21 | 5.00 |
|  | PO | 0.50 | 0.53 | 6.00 |

Observations

All the animals were found to be normal and without any clinical signs after intravenous and oral dose administration.

Sample Collection

Blood samples (approximately 60 µL) were collected from retro-orbital plexus of three mice at each time point [predose, 0.08, 0.25, 0.5, 1, 2, 4, 8 and 24 hr (IV) and predose, 0.25, 0.5, 1, 2, 4, 6, 8 and 24 hr (PO)]. During each sampling point, blood samples were collected in labeled pre-chilled tubes containing $K_2EDTA$ (20% $K_2EDTA$ solution) as an anticoagulant and protease inhibitor (10 µL of 10× solution/100 µL of blood). Low temperature was maintained till storage of plasma at −70° C. Plasma was immediately harvested from the blood by centrifugation at 4000 rpm for 10 min at 4±2° C. and stored below −70° C. until bioanalysis. Preparation of protease inhibitor solution: One tablet of sigmaFAST (Product Code: 58820) was reconstituted into 10 mL of Milli-Q water to prepare 10× solution.

Bioanalysis

Concentrations of Compound 1 in mouse plasma samples were determined by fit-for-purpose LC-MS/MS method. The sample processing and extraction procedure, chromatographic and mass spectrometric conditions are provided below:

LC Conditions

Mobile Phase A: 0.1% formic acid in Acetonitrile
  B: 0.1% formic acid in Water
Column: Phenomenex Kinetex, EVO, C18, 100×4.6 mm, 5μ
Injection Volume (μL): 5
Column Oven Temperature (° C.): 45
Retention Time (in min): Analyte: Compound 1: 1.89
  IS: Glipizide: 2.04

LC Gradient Used

| Time (Minutes) | Flow Rate (mL/min) | PUMP A (% Conc) | PUMP B (% Conc) |
|---|---|---|---|
| Initial | 0.8 | 20 | 80 |
| 1.00 | 0.8 | 95 | 5 |
| 2.20 | 0.8 | 95 | 5 |
| 2.40 | 0.8 | 20 | 80 |
| 3.20 | 0.8 | 20 | 80 |

Mass Conditions

MRM Transitions

| Analyte ID/IS ID | Q1 | Q3 | DP | CE | CXP | Dwell time (msec) |
|---|---|---|---|---|---|---|
| Compound 1 | 408.2 | 193.4 | 108 | 44 | 11 | 40 |
| Glipizide | 446.3 | 347.0 | 40 | 22 | 12 | 40 |

Source Parameter

| Polarity | Positive |
|---|---|
| CAD | 8 |
| CUR | 25 |
| GS1 | 40 |
| GS2 | 60 |
| Ion Spray Voltage | 5500 |
| Temperature | 550 |
| Interface Heater | ON |
| EP | 10 |

Extraction Procedure

The extraction procedure for plasma samples and the spiked plasma calibration standards were identical:

A 25 μL of study sample (DF was applied for few samples) or spiked plasma calibration standard was added to individual pre-labeled micro-centrifuge tubes followed by 100 μL of internal standard prepared in acetonitrile (Glipizide, 500 ng/mL) was added except for blank, where 100 μL of acetonitrile was added. Samples were vortexed for 5 minutes. Samples were centrifuged for 10 minutes at a speed of 4000 rpm at 4° C. Following centrifugation, 100 μL of clear supernatant was transferred in 96 well plates and analyzed using LC-MS/MS.

Data Analysis

Non-Compartmental-Analysis tool of Phoenix WinNonlin® (Version 6.3) was used to assess the pharmacokinetic parameters. Peak plasma concentration ($C_{max}$) and time for the peak plasma concentration ($T_{max}$) were the observed values. The areas under the concentration time curve ($AUC_{last}$ and $AUC_{inf}$) were calculated by linear trapezoidal rule. The terminal elimination rate constant, ke was determined by regression analysis of the linear terminal portion of the log plasma concentration-time curve. The terminal half-life ($T_{1/2}$) was estimated by 0.693/ke; $CL_f=Dose/AUC_{inf}$; $V_z=MRT \times CL_F$.

Results

Following a single intravenous dose administration of Compound 1 to male BALB/c mice, compound showed low plasma clearance (11.20 mL/min/kg; normal liver blood flow in mice is 90 mL/min/kg) with terminal elimination half-life of 4.24 hr. The Vss was ~2-fold more than normal volume of total body water (0.7 L/kg). Following a single oral administration of Compound 1 to male BALB/c mice at 5 mg/kg, plasma concentrations were quantifiable up to 24 hr (2 animals out of 3) with $T_{max}$ at 0.25 hr. Oral solution bioavailability was 42%.

TABLE 2

Pharmacokinetic parameters of Compound 1 in plasma following a single intravenous (Dose: 1 mg/kg) and oral (Dose: 5 mg/kg) administration in male BALB/c mice

| Route | Dose (mg/kg) | $T_{max}$ (hr) | [a]$C_o/C_{max}$ (ng/mL) | $AUC_{last}$ (hr * ng/mL) | $AUC_{inf}$ (hr * ng/mL) | $T_{1/2}$ (hr) | CL (mL/min/kg) | $V_{ss}$ (L/kg) | % F[b] |
|---|---|---|---|---|---|---|---|---|---|
| IV | 1 | — | 2747.53 | 1480.60 | 1487.95 | 4.24 | 11.20 | 1.20 | — |
| PO | 5 | 0.25 | 1856.61 | 3108.35 | 3116.66 | 3.26 | 26.74 | 7.55 | 42 |

*$T_{1/2}$ expressed as $T_{1/2z}$, CL expressed as $CL_f$ and $V_{ss}$ expressed as $V_z$ for PO group

[a] back extrapolated conc. for i.v. group;

[b] $AUC_{last}$ was considered for calculating oral bioavailability

TABLE 3

Individual plasma concentration-time data of Compound 1 following a single intravenous administration in male BALB/c mice (Dose: 1 mg/kg)

| Animal ID | Pre-dose | 0.08 | 0.25 | 0.5 | 1 | 2 | 4 | 8 | 24 |
|---|---|---|---|---|---|---|---|---|---|
| 1 | 0.00 | | | 899.26 | | | 37.94 | | |
| 2 | 0.00 | | | 894.59 | | | 27.10 | | |
| 3 | 0.00 | | | 951.53 | | | 39.18 | | |
| 4 | | 1220.50 | | | 151.52 | | | 6.59 | |
| 5 | | 2541.20 | | | 496.44 | | | 27.95 | |
| 6 | | 2233.92 | | | 268.90 | | | 8.94 | |
| 7 | | | 947.97 | | | 42.55 | | | 1.36 |
| 8 | | | 1052.34 | | | 60.16 | | | 1.10 |
| 9 | | | 1048.27 | | | 49.49 | | | 0.00 |
| Mean | 0.00 | 1998.54 | 1016.19 | 915.13 | 305.62 | 50.73 | 34.74 | 14.49 | 1.23[d] |
| SD | 0.00 | 691.10 | 59.12 | 31.61 | 175.37 | 8.87 | 6.65 | 11.71 | NA |
| CV % | NA | 34.6 | 5.8 | 3.5 | 57.4 | 17.5 | 19.1 | 80.8 | NA |

LLOQ = 1.02 ng/mL;
NA not applicable;
[d]Average of two values considered for data analysis.
Values below LLOQ or no peaks were considered zero.

TABLE 4

Individual plasma concentration-time data of Compound 1 following a single oral administration in male BALB/c mice (Dose: 5 mg/kg)

| Animal ID | Pre-dose | 0.25 | 0.5 | 1 | 2 | 4 | 6 | 8 | 24 |
|---|---|---|---|---|---|---|---|---|---|
| 10 | 0.00 | | | 474.33 | | | 110.77 | | |
| 11 | 0.00 | | | 433.52 | | | 81.54 | | |
| 12 | 0.00 | | | 462.13 | | | 83.17 | | |
| 13 | | 1692.48 | | | 534.93 | | | 42.97 | |
| 14 | | 2450.80 | | | 331.78 | | | 41.28 | |
| 15 | | 1426.54 | | | 365.08 | | | 53.22 | |
| 16 | | | 2167.46 | | | 86.92 | | | 0.00 |
| 17 | | | 1898.77 | | | 503.47 | | | 1.28 |
| 18 | | | 1070.15 | | | 59.61 | | | 2.31 |
| Mean | 0.00 | 1856.61 | 1712.13 | 456.66 | 410.60 | 216.67 | 91.83 | 45.82 | 1.80[d] |
| SD | 0.00 | 531.49 | 571.97 | 20.95 | 108.96 | 248.75 | 16.43 | 6.46 | NA |
| CV % | NA | 28.6 | 33.4 | 4.6 | 26.5 | 114.8 | 17.9 | 14.1 | NA |

LLOQ = 1.02 ng/mL;
NA not applicable;
[d]Average of two values considered for data analysis.
Values below LLOQ or no peaks were considered zero.

The abbreviations used in this study are
ACN: Acetonitrile
LLOQ: Lower Limit of Quantitation
CV: Coefficient of Variation
IS: Internal Standard
IV: Intravenous
LC-MS/MS: Liquid Chromatography Mass Spectrometry
NA: Not Applicable
PO: Per oral
SD: Standard Deviation
SOP: Standard Operating Procedure
$C_{max}$: Maximum concentration
$T_{max}$: Time to reach maximum concentration
AUC: Area under Plasma concentration—Time curve
CL: Clearance
Vss: Volume of distribution
$T_{1/2}$: Half life
% F: Bioavailability.

The invention claimed is:

1. A compound of the following formula:

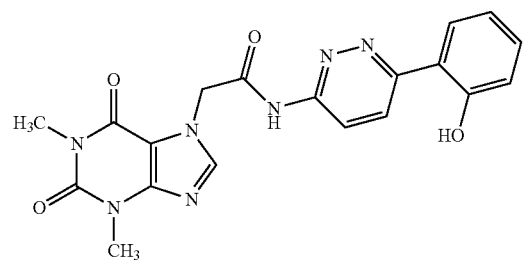 [SMILES: Cn1c(=O)c2c(ncn2CC(=O)Nc2ccc(-c3ccccc3O)nn2)n(C)c1=O]

or a pharmaceutically acceptable salt thereof.

2. A medicament comprising the compound according to claim 1, or a pharmaceutically acceptable salt thereof.

3. A pharmaceutical composition comprising one or more pharmaceutically acceptable adjuvants, carriers, or diluents and the compound according to claim 1, or a pharmaceutically acceptable salt thereof.

4. A method for modulating porcupine activity in a cell, comprising exposing the cell to the compound according to claim 1, or a pharmaceutically acceptable salt thereof.

5. A method for modulating Wnt secretion in a cell, comprising exposing the cell to the compound according to claim 1, or a pharmaceutically acceptable salt thereof.

6. A method for modulating Wnt pathway activity in a subject, comprising administering to a subject in need thereof a therapeutically effective amount of the compound according to claim 1, or a pharmaceutically acceptable salt thereof.

7. The method according to claim 6, wherein the subject has a disease or condition associated with Wnt pathway activity selected from the group consisting of a cancer, a degenerative disease, a fibrotic disease, and a metabolic disease.

8. The method according to claim 7, wherein the cancer is characterized by high Wnt pathway activity.

9. The method according to claim 7, wherein the cancer is selected from the group consisting of basal cell carcinoma, bladder cancer, breast cancer, cervical cancer, chronic lymphocytic leukemia, colon cancer, gastric cancer, head and neck cancer, hepatocellular carcinoma, lung cancer, medulloblastoma, melanoma, mesothelioma, osteosarcoma, ovarian cancer, pancreatic adenocarcinoma, prostate cancer, and thyroid cancer.

10. The method according to claim 9, wherein the lung cancer is non-small-cell lung cancer.

11. The method according to claim 7, wherein the fibrotic disease is selected from the group consisting of liver fibrosis, pulmonary fibrosis, renal fibrosis, and skin fibrosis.

12. The method according to claim 7, wherein the metabolic disease is diabetic retinopathy.

13. A compound of the following formula:

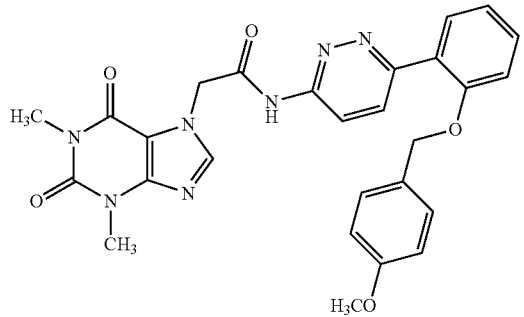 [SMILES: COc1ccc(COc2ccccc2-c2ccc(NC(=O)Cn3cnc4c3c(=O)n(C)c(=O)n4C)nn2)cc1]

or a pharmaceutically acceptable salt thereof.

* * * * *